(12) United States Patent
Noble et al.

(10) Patent No.: US 9,192,327 B2
(45) Date of Patent: Nov. 24, 2015

(54) BLOOD COLLECTION DEVICE WITH TUBE RETAINING STRUCTURE

(75) Inventors: Michael J. Noble, St. Charles, MO (US); Todd M. Chelak, Westborough, MA (US)

(73) Assignee: Covidien LP, Mansfield, MA (US)

(*) Notice: Subject to any disclaimer, the term of this patent is extended or adjusted under 35 U.S.C. 154(b) by 230 days.

(21) Appl. No.: 13/248,868

(22) Filed: Sep. 29, 2011

(65) Prior Publication Data

US 2012/0022403 A1 Jan. 26, 2012

Related U.S. Application Data

(63) Continuation of application No. 12/333,526, filed on Dec. 12, 2008, now abandoned.

(60) Provisional application No. 61/007,639, filed on Dec. 14, 2007.

(51) Int. Cl.
| | |
|---|---|
| *A61B 5/00* | (2006.01) |
| *B65D 81/00* | (2006.01) |
| *A61B 17/14* | (2006.01) |
| *A61B 17/32* | (2006.01) |
| *A61B 5/15* | (2006.01) |
| *A61B 5/154* | (2006.01) |

(52) U.S. Cl.
CPC .............. *A61B 5/1438* (2013.01); *A61B 5/1405* (2013.01); *A61B 5/1444* (2013.01); *A61B 5/15* (2013.01); *A61B 5/154* (2013.01)

(58) Field of Classification Search
CPC ........ A61B 5/15; A61B 5/154; A61B 5/1405; A61B 5/1438; A61B 5/1444
USPC ................... 600/573, 577, 583; 606/181, 182
See application file for complete search history.

(56) References Cited

U.S. PATENT DOCUMENTS

| | | | | |
|---|---|---|---|---|
| 3,366,103 | A | * | 1/1968 | Keller ........................... 600/577 |
| 4,150,666 | A | | 4/1979 | Brush |
| 4,280,509 | A | * | 7/1981 | Bethkenhagen et al. ...... 600/579 |
| 4,295,476 | A | * | 10/1981 | Quaas ........................... 600/577 |
| 4,320,769 | A | * | 3/1982 | Eichhorn et al. .............. 600/576 |
| 4,331,147 | A | * | 5/1982 | Armstrong .................... 604/317 |
| 4,808,381 | A | | 2/1989 | McGregor et al. |

(Continued)

FOREIGN PATENT DOCUMENTS

| | | |
|---|---|---|
| EP | 0342653 A2 | 11/1989 |
| EP | 1782732 A1 | 5/2007 |
| WO | 2007134347 A2 | 11/2007 |

OTHER PUBLICATIONS

European Search Report regarding related application serial No. EP 08171487.5 dated Apr. 29, 2009—6 pgs.

(Continued)

*Primary Examiner* — Devin Henson
(74) *Attorney, Agent, or Firm* — Lisa E. Winsor, Esq.

(57) ABSTRACT

A blood collection device is disclosed which includes a body defining a receptacle dimensioned to receive a blood collection tube. The body has a first open end and a second end supporting a needle having a proximal end extending into the receptacle and a distal end extending distally of the body. Retaining structure is supported on the body. The retaining structure extends into the receptacle and is configured to releasably retain the blood collection tube within the receptacle.

20 Claims, 5 Drawing Sheets

(56) References Cited

U.S. PATENT DOCUMENTS

| | | | | |
|---|---|---|---|---|
| 4,915,702 A * | 4/1990 | Haber | | 604/198 |
| 4,984,580 A | 1/1991 | Wanamaker | | |
| 4,991,601 A * | 2/1991 | Kasai et al. | | 600/576 |
| 5,000,167 A | 3/1991 | Sunderland | | |
| RE33,585 E | 5/1991 | Haber et al. | | |
| 5,086,783 A | 2/1992 | Macors et al. | | |
| 5,188,119 A | 2/1993 | Sunderland | | |
| 5,267,983 A | 12/1993 | Oilschlager et al. | | |
| 5,344,417 A | 9/1994 | Wadsworth, Jr. | | |
| 5,358,501 A | 10/1994 | Meyer | | |
| 5,360,012 A * | 11/1994 | Ebara et al. | | 600/577 |
| 5,360,423 A | 11/1994 | McCormick | | |
| 5,374,264 A | 12/1994 | Wadsworth, Jr. | | |
| 5,487,737 A | 1/1996 | Meyer | | |
| 5,776,124 A | 7/1998 | Wald | | |
| 5,893,397 A | 4/1999 | Peterson et al. | | |
| 6,755,804 B2 * | 6/2004 | Crawford | | 604/110 |
| 6,837,872 B2 | 1/2005 | Crawford | | |
| 7,261,698 B2 | 8/2007 | Sampson et al. | | |
| 7,736,322 B2 | 6/2010 | Roe et al. | | |

OTHER PUBLICATIONS

European Search Report regarding related application serial No. EP 10196380.9 dated Mar. 24, 2011—6 pgs.

Office action dated Dec. 30, 2009 from related U.S. Appl. No. 12/333,526—10 pgs.

Response filed Mar. 26, 2010 to Office Action dated Dec. 30, 2009 regarding related U.S. Appl. No. 12/333,526—18 pgs.

Office action dated May 26, 2010 from related U.S. Appl. No. 12/333,526—16 pgs.

Response filed Jul. 26, 2010 to Office Action dated May 26, 2010 regarding related U.S. Appl. No. 12/333,526—10 pgs.

Advisory Action issued Jul. 30, 2010 from related U.S. Appl. No. 12/333,526—3 pgs.

Response filed Aug. 18, 2010 to Advisory Action issued Jul. 30, 2010 regarding related U.S. Appl. No. 12/333/526—10 pgs.

Advisory Action issued Aug. 23, 2010 from related U.S. Appl. No. 12/333,526—3 pgs.

Response filed Oct. 25, 2010 to Advisory Action issued Aug. 23, 2010 regarding related U.S. Appl. No. 12/333,526—10 pgs.

Advisory Action issued Nov. 4, 2010 from related U.S. Appl. No. 12/333,526—3 pgs.

Response filed Dec. 8, 2010 to Advisory Action issued Nov. 4, 2010 regarding related U.S. Appl. No. 12/333,526—7 pgs.

Advisory Action issued Dec. 16, 2010 from related U.S. Appl. No. 12/333,526—3 pgs.

Appeal Brief filed Dec. 26, 2010 in response to Office action issued May 26, 2010 in related U.S. Appl. No. 12/333,526—20 pgs.

* cited by examiner

BLOOD COLLECTION DEVICE WITH TUBE RETAINING STRUCTURE

CROSS-REFERENCE TO RELATED APPLICATIONS

The present application is a continuation of U.S. patent application Ser. No. 12/333,526, filed on Dec. 12, 2008, which claimed priority to U.S. Provisional Patent Application No. 61/007,639, filed on Dec. 14, 2007, both of which are incorporated herein by reference in their entireties.

BACKGROUND

1. Technical Field

The present disclosure relates to the field of medical fluid transfer devices and, more particularly, to devices for safely transferring bodily fluids to a receptacle.

2. Description of Related Art

In the medical field, fluid transfer devices, particularly, blood collection devices are used to draw blood from patients for blood tests and other medical procedures. At all times, phlebotomists have to be careful of the being exposed to life-threatening bloodborne pathogens (BBP) such as HIV and hepatitis.

Blood collection devices are well known in the medical field and typically include a body defining a receptacle which is dimensioned to receive a blood collection tube. The body includes an open proximal end and a distal end, which supports a needle. The needle has a distal end extending from the distal end of the body and a proximal end extending into the receptacle. The proximal end of the needle positioned within the receptacle is covered by a flexible valve member which is provided to reseal the proximal end of the needle after a blood collection tube has been removed from the receptacle.

In use during a blood draw procedure, a phlebotomist will insert the distal end of the needle into a patient's vein. Thereafter, the phlebotomist will insert a blood collection tube into the receptacle of the blood collection device. Generally, the blood collection tube includes a pierceable septum such that when the tube is inserted into the receptacle, the proximal end of the needle will engage the septum and pierce both the valve member and the septum. As the tube is pressed into the receptacle, the valve member is compressed distally about the needle.

The valve member is formed from a resilient material, which will return to a position to seal the proximal end of the needle when the blood collection tube is removed from the receptacle. When the valve member is in a compressed state, the valve member tends to urge the blood collection tube from the receptacle of the blood collection device, which results in slowing or stopping the blood flow into the blood collection tube. To prevent or ensure that a blood collection tube is not pushed from the valve member, medical personnel may have to grip the blood collection tube while holding the blood collection device in position. If a blood collection tube were to become disengaged from a blood collection device, it is likely that the tube would break and blood would be spilled exposing medical personnel to the dangers of BBP's and also broken glass.

Accordingly, it would be useful and beneficial, in the art of medical devices, for an inexpensive, simple device capable of securing and holding a blood collection tube, or the like, within the receptacle of a blood collection device.

SUMMARY

A blood collection device is disclosed which includes a body defining a receptacle dimensioned to receive a blood collection tube. The body has a first open end and a second end supporting a needle having a proximal end extending into the receptacle and a distal end extending distally of the body. Retaining structure is supported on the body. The retaining structure extends into the receptacle and is configured to releasably retain the blood collection tube within the receptacle. In one embodiment, the retaining structure is integrally formed with the body defining the receptacle and includes at least one arm pivotally supported on the body and configured to engage a blood collection tube positioned within the receptacle. The at least one arm may include a pair of spaced arms. In one embodiment, each of the at least one arms includes a surface positioned to engage a blood collection tube which is slip-resistant. The slip-resistant surface may be textured, e.g., ratchet teeth, granules, serrations, knurling, etc. Alternately, the slip-resistant surface may include an elastomeric layer of material.

In one embodiment, the retaining structure includes at least one finger nub. Each of the at least one finger nubs is connected to one of the at least one arms by a pivot member and is actuable to disengage the at least one arm from engagement with a blood collection tube positioned within the receptacle of the body. The retaining structure may include one or more teeth which are configured to engage the blood collection tube.

In one embodiment, the retaining structure is supported on an inner surface of the body defining the receptacle. The retaining structure may include at least one resilient biasing member disposed on an inner surface of the body. The at least one resilient biasing member has first and second ends secured to the inner surface of the body such that a central portion of the at least one resilient biasing member bows inwardly from the inner surface of the body into the receptacle.

BRIEF DESCRIPTION OF THE DRAWINGS

Various embodiments of the presently disclosed medical access device are disclosed herein with reference to the drawings, wherein.

DETAILED DESCRIPTION

Figure 1:
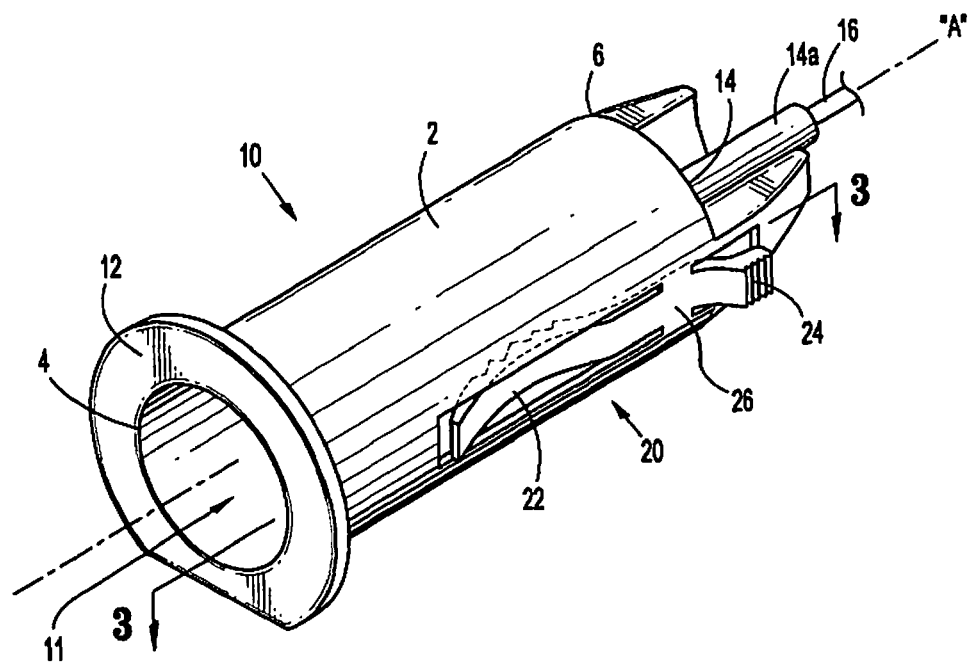
FIG. 1 is a perspective view of one embodiment of the presently disclosed blood collection device.
Figure 2:
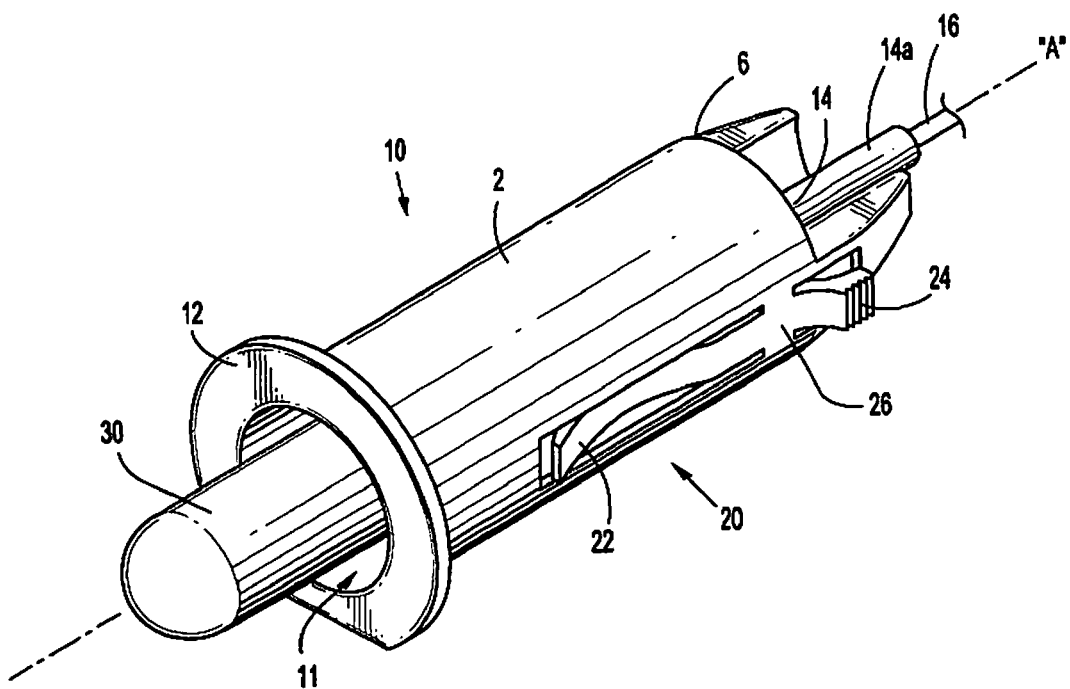
FIG. 2 is a perspective view of the blood collection device shown in FIG. 1 with a blood collection tube inserted therein.

Embodiments of the presently disclosed medical device will now be described in detail with reference to the drawings wherein like reference numerals designate identical or corresponding elements in each of the several views. In the discussion that follows, the term "proximal" refers to a portion of a structure that is closer to a user, and the term "distal" refers to a portion that is further from the user.

Referring initially to FIGS. 1-5, a medical blood collector is provided, which includes a blood collection device 10 having a substantially tubular housing 2 defining a receptacle 11. Housing 2 includes a proximal open end 4 and a distal end 6 having a hub 14 disposed thereon. A finger flange 12 is provided on the proximal end 4 of housing 2 to facilitate insertion of a blood collection tube 30 into receptacle 11. Proximal open end 4 is configured and dimensioned to allow a blood collection tube 30 to be inserted therethrough.

Hub 14 defines a channel (not shown) for receiving and securing a transfer needle 34 and patient needle 16 to housing 2 of blood collection device 10. Transfer needle 34 extends proximally from hub 14 into receptacle 11. Patient needle 16 extends distally from hub 14 to a location distally of housing 2. In one embodiment, transfer needle 34 and patient needle 16 are manufactured in a one-piece configuration as a double-ended needle. Alternatively, transfer needle 34 and patient needle 16 may be manufactured in a multiple-piece construction and maintained in fluid communication with each other through hub 14. It is also contemplated that transfer needle 34 and patient needle 16 or the one-piece needle equivalent may be secured to a needle hub which is received by and attached to hub 14.

A resealable valve member 36 is positioned over transfer needle 34 to seal transfer needle 34 when a blood collection tube 30 is not positioned within receptacle 11. Resealable valve member 36 is formed from a resilient, pierceable material.

Patient needle 16 is configured to pierce through a patient's blood vessel to perform a blood draw procedure. Transfer needle 34 and patient needle 16 are in fluid communication to allow blood flow from the patient's blood vessel to transfer needle 34. When blood collection tube 30 is longitudinally inserted into proximal end 4 of housing 2 towards distal closed end 6 of housing 2, transfer needle 34, which has a sharpened proximal end 34a, pierces a pierceable septum 32 of blood collection tube 30 to allow blood to flow from transfer needle 34 into blood collection tube 30.

Figure 5:
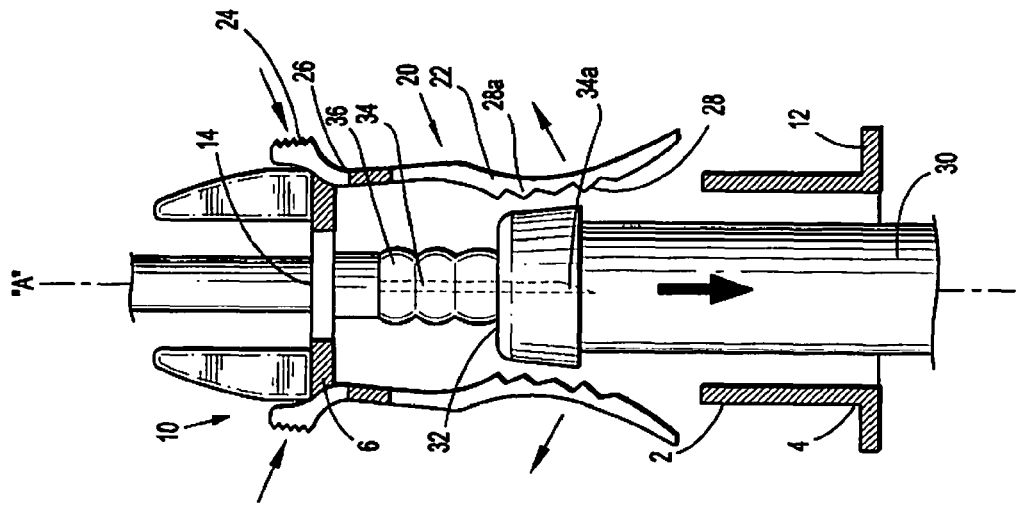
FIG. 5 is a side cross-sectional view of the blood collection device shown in FIG. 2 as the blood collection tube is removed therefrom.
Figure 4:
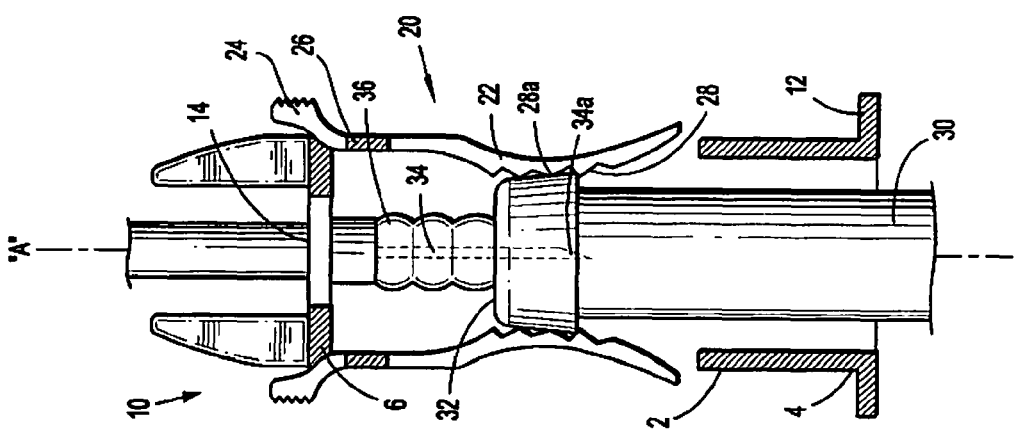
FIG. 4 is a side cross-sectional view of the blood collection device shown in FIG. 2 with the blood collection tube inserted therein.
Figure 3:
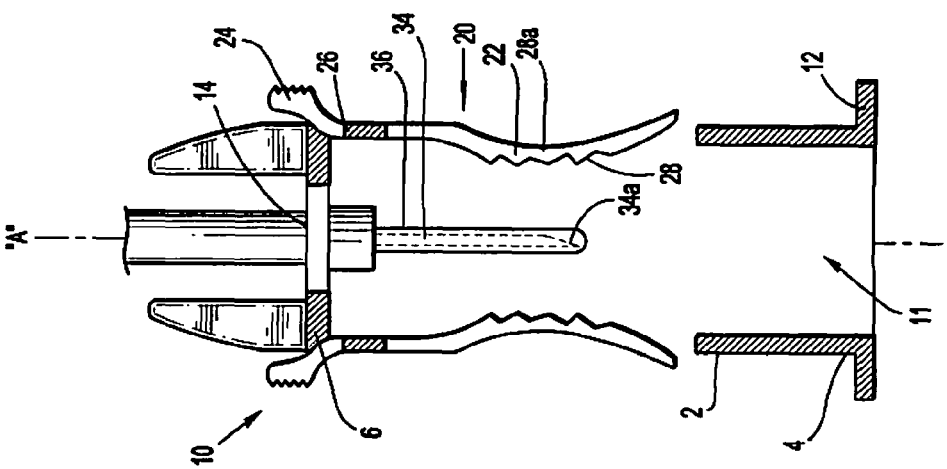
FIG. 3 is a side cross-sectional view of the blood collection device shown in FIG. 1 taken along section lines 3-3.

Referring also to FIGS. 3-5, blood collection device 10 includes retaining structure 20. Embodiments of the presently disclosed blood collection device 10 include one or more substantially identical retaining structures. For purposes of brevity, only one retaining structure will be explained in detail.

Retaining structure 20 is configured and dimensioned to releasably retain a blood collection tube 30 within receptacle 11 of blood collection device 10. Retaining structure 20 includes a retaining arm 22 and a finger actuation member or nub 24, which are integrally formed with receptacle 11. Retaining arm 22 and finger nub 24 are pivotably connected at a pivot member 26, which is also integrally formed with receptacle 11. Retaining arm 22 includes an inner surface 28 which defines a portion of a wall of receptacle 11 and is configured to retain blood collection tube 30 within receptacle 11. Inner surface 28 of retaining arm 22 may be constructed from any type of suitable gripping surface, e.g., ratchet teeth, elastomeric material, granular material, etc., suitable to retain and/or engage a blood collection tube 30.

As depicted in FIGS. 3-5, one or more ratchet teeth 28a are disposed on inner surface 28 of retaining arm 22 and are configured to allow substantially non-resistive movement in the insertion direction, but prevent movement in the removal direction. Ratchet teeth 28a may have a different slope on proximal and distal sides of each tooth to effect this result. Retaining arm 22 is configured to be biased in an inward direction towards longitudinal axis "A" of receptacle 11 such that ratchet teeth 28a engage blood collection tube 30 to retain tube 30 within receptacle 11 (FIG. 4). Arms 22 may be biased inwardly due to the natural resilience of the material used to construct arms 22, e.g., plastic, or alternatively, a biasing member, e.g., spring steel, may be secured to arms 22 to provide a biasing force. When medical personnel desire to remove tube 30 from receptacle 11, finger nub 24 can be pressed inwardly to pivot retaining arm 22 about pivot member 26 outwardly out of engagement with tube 30 (FIG. 5).

In summary, as blood collection tube 30 is inserted into receptacle 11 of device 10, transfer needle 34 pierces valve member 36 and pierceable septum 32 of blood collection tube 30. As blood collection tube 30 is longitudinally moved towards distal end 6 of receptacle 11, valve member 36 compresses and creates a biasing effect, thus urging blood collection tube 30 out of receptacle 11. Ratchet teeth 28a of retaining structure 20 are dimensioned and configured to engage and retain blood collection tube 30 within receptacle 11 of device 10.

As mentioned above, blood collection tube 30 is removed from receptacle 11, as shown in FIG. 5, by pushing finger nub 24 inwards towards the longitudinal axis of device 10. When this occurs, retaining arm 22 is pivoted about living hinge 26 to pivot retaining arm 22 outwardly to disengage ratchet teeth 28a from blood collection tube 30. As this occurs, the user can pull on the blood collection tube 30 to remove tube 30 from receptacle 11.

Figure 7:
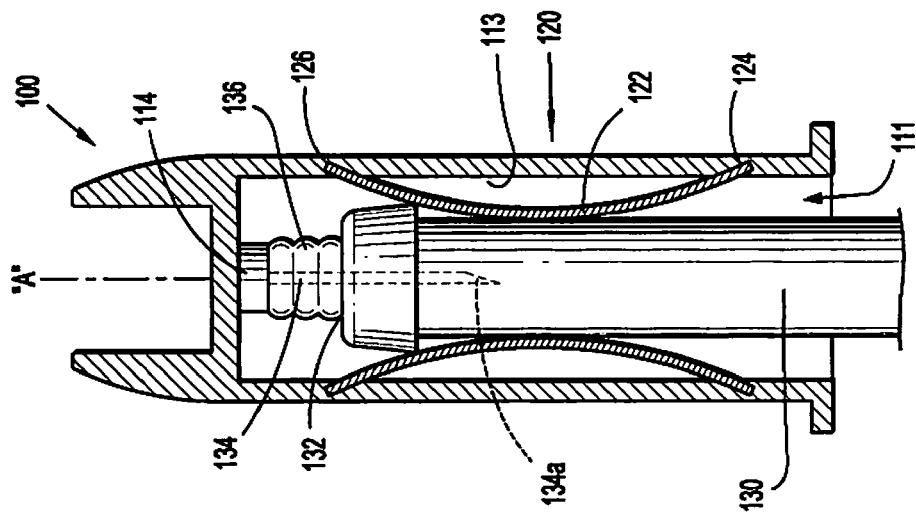
FIG. 7 is a side cross-sectional view of the blood collection device shown in FIG. 6 with a blood collection tube inserted therein.
Figure 6:
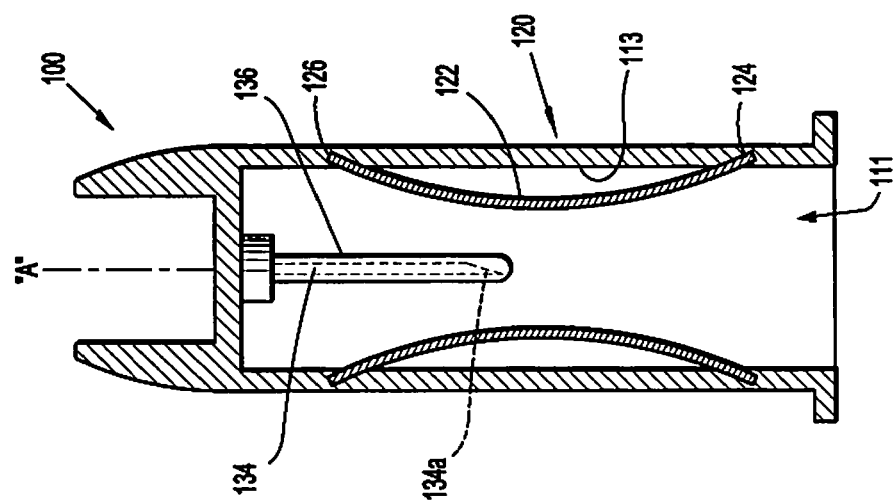
FIG. 6 is a side cross-sectional view of another embodiment of the presently disclosed blood collection device.

FIGS. 6 and 7 illustrate another embodiment of the presently disclosed blood collection device shown generally as 100. Blood collection device 100 defines a receptacle 111 and includes a transfer needle 134 and a valve member 136, which function in the same manner as the like elements described above. Collection device 100 also includes a patient needle (not shown) which can be fixedly secured to device 100, removably secured to device 100 using, for example, a luer type connector, or otherwise attached to device 100 in combination with transfer needle 134 as described previously. Retaining structure 120 includes a biasing member 122 disposed on inner surface 113 of receptacle 111. Biasing member 122 may be composed of a resilient metal strip, or any suitable biasing material known in the art. Biasing member 122 includes a first end 124 and a second end 126. First and second ends, 124 and 126, respectively, are secured to a side wall 113 of receptacle 111 such that a central portion of member 122 bows into receptacle 111. It is also contemplated that biasing member 122 may be secured to side wall 113 by only first end 124 or second end 126 of biasing member 122.

In use, as shown in FIG. 7, blood collection tube 130 is inserted longitudinally into receptacle 111. Biasing members 122 of retaining structure 120 are configured to provide a smaller diameter to engage and retain tube 130 within receptacle 111. A tube engaging surface of retaining structure 120 may comprise a textured surface (e.g., serrated, granular, tacky, etc.) to more securely engage tube 130 and prevent slippage of tube 130 in relation to biasing members 122. Retaining structure 120 may also be configured and adapted to retain different shapes and sizes of blood collection tubes within receptacle 111, i.e., retaining members 122 may be dimensioned and configured to retain tubes having a variety of different shapes within receptacle 111 of device 100.

Figure 8:
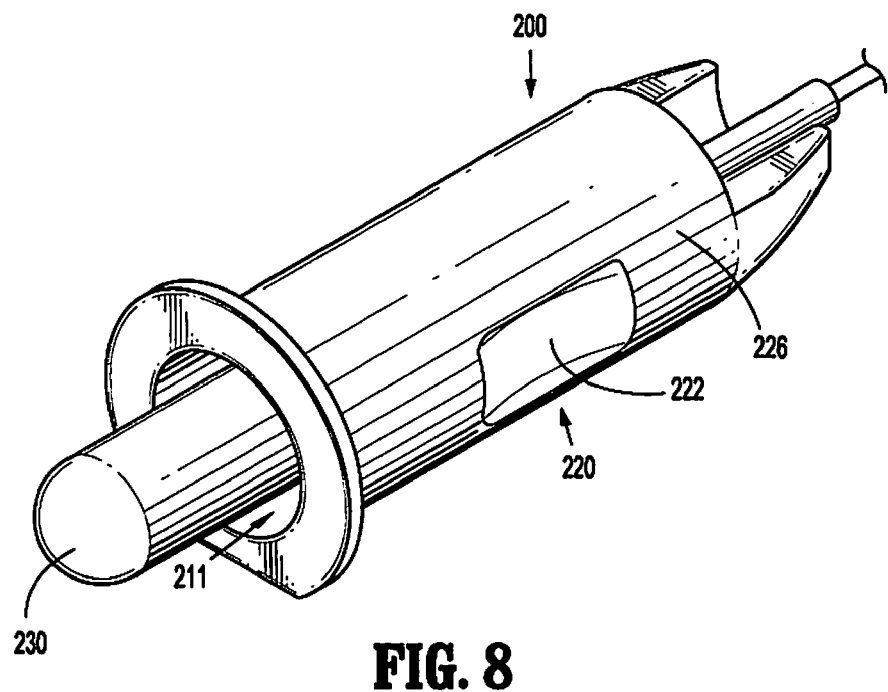
FIG. 8 is a perspective view of another embodiment of the presently disclosed blood collection device with a blood collection tube inserted therein.
Figure 9:
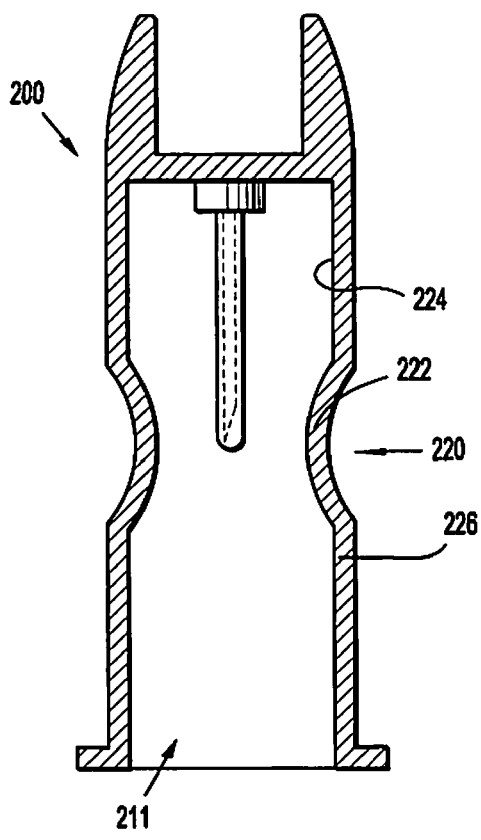
FIG. 9 is a side cross-sectional view of the blood collection device shown in FIG. 8 with the blood collection tube removed.
Figure 10:
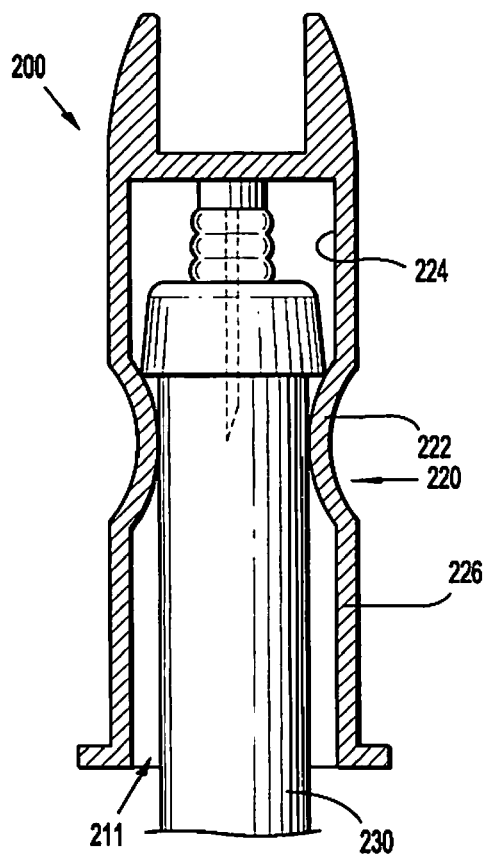
FIG. 10 is a side cross-sectional view of the blood collection device shown in FIG. 8 with the blood collection tube inserted therein.

As shown in FIGS. 8-10, in another embodiment of blood collection device 200 retaining structure 220 defines one or more resilient bump-like raised inner wall portions 222 (i.e., one, two, three, four, etc.) alongside inner wall 224 of device 200. Retaining structure 220 provides a smaller inner diameter of receptacle 211 to secure a blood collection tube 230 within receptacle 211. The wall thickness of raised wall 222 may be thinner than surrounding inner wall 224 to facilitate engagement with blood tube 230. The raised wall 222 may be formed during a forming process (e.g., an injection molding process or a deformation process) and/or by a forming device.

In one embodiment, the forming device may be a heating element (not shown) that is configured to heat the outside wall 226 of receptacle 211 to form indentations in outside wall 226 of receptacle 211 and thus, form raised-wall 222 along the internal wall of device 200. In other embodiments, the forming device may be a roller-type element (not shown) having, for example, a star-shaped element. Alternatively, the forming device may be a collet (not shown) with forming detents on an inner diameter of the collet.

Figure 12:
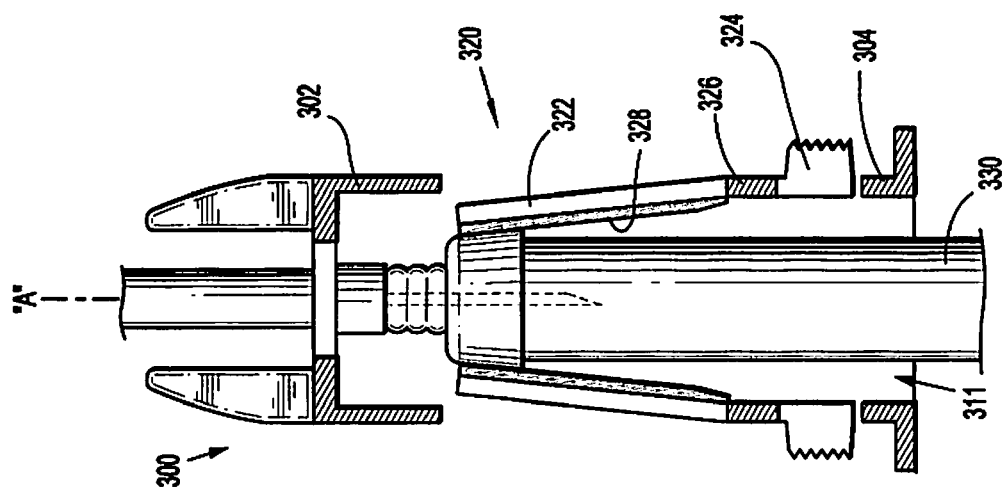
FIG. 12 is a side cross-sectional view of the blood collection device shown in FIG. 11 with a blood collection tube inserted therein.
Figure 11:
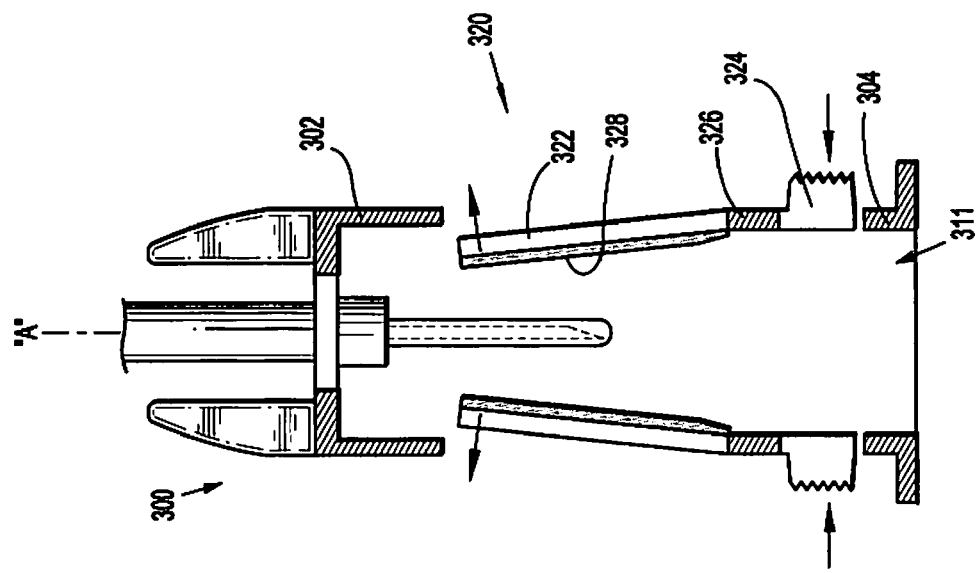
FIG. 11 is a side cross-sectional view of yet another embodiment of the presently disclosed blood collection device.

FIGS. 11 and 12 illustrate another embodiment of the presently disclosed blood collection device shown generally as 300. Blood collection device 300 includes a tubular shaped body 302 defining a receptacle 311 having a proximal and distal ends 304 and 306, respectively. Body 302 includes a retaining structure 320 having a retaining arm 322 and finger member or nub 324. Retaining arm 322 and finger nub 324 are pivotably connected to body 302 at a living hinge 326, which is located on proximal side 304 of body 302.

Blood collection tube 330 is retained within the receptacle 311 by retaining arms 322 of retaining structure 320. Retaining arms 322 include an elastomeric coating on an inner surface 328 of retaining arms 322 positioned to frictionally engage blood collection tube 330 located within receptacle 311. The elastomeric coating on inner surface 328 provides a tight, non-slip surface for releasably retaining blood collection tube 330 within receptacle 311 (FIG. 12). In one embodiment, the elastomeric coating is overmolded onto arms 322. Alternately, other techniques can be used to secure the elastomeric coating to the arms 322 of retaining structure 320.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A blood collection device, comprising a body including a housing having a sidewall forming a receptacle sized and shaped to receive a blood collection tube, the body including a closed distal end having a needle extending proximally into the receptacle, an open proximal end opposite the closed end for receiving the collection tube as the tube enters the receptacle and a retaining arm extending proximally from a distal end connected to the sidewall of the housing at a location spaced from the closed distal end to a proximal end free from the housing, a portion of the retaining arm spaced proximally of the distal end of the retaining arm extending into the receptacle, a central portion of the retaining arm bowing inwardly from an inner surface of the housing into the receptacle, the central portion extending farther into the receptacle than the remainder of the retaining arm, the retaining arm being configured to retain the blood collection tube against proximal movement when the blood collection tube is received in the receptacle, wherein the central portion engages the blood collection tube to retain the blood collection tube when the blood collection tube is fully inserted into the receptacle.

2. A blood collection device as set forth in claim 1, wherein the needle extends distally from the distal end of the body.

3. A blood collection device as set forth in claim 1, wherein the retaining arm is integrally formed with the body.

4. A blood collection device as set forth in claim 1, wherein the retaining arm includes a tooth configured to engage the blood collection tube.

5. A blood collection device as set forth in claim 1, wherein the retaining arm is a first retaining arm, and the blood collection device includes a second retaining arm spaced from said first retaining arm.

6. A blood collection device as set forth in claim 1, wherein the arm includes a slip-resistant surface positioned to engage the blood collection tube.

7. A blood collection device as set forth in claim 6, wherein the slip-resistant surface is textured.

8. A blood collection device according to claim 7, wherein the textured slip-resistant surface is selected from the group consisting of ratchet teeth, granules, serrations, and knurling.

9. A blood collection device according to claim 7, wherein the slip-resistant surface includes an elastomeric layer of material.

10. A blood collection device, comprising a body including a housing forming a receptacle sized and shaped to receive a blood collection tube, the body including a closed distal end having a needle extending proximally into the receptacle, an open proximal end opposite the closed end for receiving the collection tube as the tube enters the receptacle and a retaining arm extending into the receptacle from a distal end connected to the housing to a position inside the receptacle, the retaining arm having a distal portion, a proximal portion opposite the distal portion, and a central portion between the distal and proximal portions that is separate from an inner surface of the housing, the central portion of the retaining arm bowing inwardly from the inner surface of the housing into the receptacle, in which an inner engagement surface on the central portion of the arm selectively engages the blood collection tube when the blood collection tube is fully inserted into the receptacle, the inner engagement surface of the arm being adapted to provide increased frictional engagement of the blood collection tube compared to the distal and proximal portions of the arm, the inner engagement surface on the central portion extending farther into the receptacle than the remainder of the retaining arm.

11. A blood collection device as set forth in claim 10, wherein the retaining arm includes a tooth configured to engage the blood collection tube.

12. A blood collection device as set forth in claim 10, wherein the retaining arm is a first retaining arm, and the blood collection device includes a second retaining arm spaced from said first retaining arm.

13. A blood collection device as set forth in claim 10, wherein the inner engagement surface is textured.

14. A blood collection device according to claim 13, wherein the textured inner engagement surface is selected from the group consisting of ratchet teeth, granules, serrations, and knurling.

15. A blood collection device according to claim 13, wherein the inner engagement surface includes an elastomeric layer of material.

16. A blood collection device, comprising a body forming a receptacle sized and shaped to receive a blood collection tube, the body having an end supporting a needle extending into the receptacle and an open end opposite the needle supporting end, and a retaining structure including a retaining arm pivotally supported on one end and a finger nub operably connected to the arm, the retaining arm being resiliently biased into the receptacle, such that the retaining arm is located within the receptacle in its natural unstressed configuration, and the finger nub being depressible to pivot the retaining arm outward from the receptacle to releasably retain the blood collection tube in the receptacle, the retaining arm being connected to the body at a distal end, a central portion of the retaining arm bowing inwardly from an inner surface of the body into the receptacle, the central portion extending farther into the receptacle than the remainder of the retaining arm, the retaining arm being configured to retain the blood collection tube against proximal movement when the blood collection tube is received in the receptacle, wherein the central portion of the retaining arm extending the farthest into the receptacle engages the blood collection tube to retain the blood collection tube when the blood collection tube is fully inserted into the receptacle.

17. A blood collection device as set forth in claim 16, wherein the retaining arm includes a tooth configured to engage the blood collection tube.

18. A blood collection device as set forth in claim 16, wherein the retaining arm is a first retaining arm, and the blood collection device includes a second retaining arm spaced from said first retaining arm.

19. A blood collection device as set forth in claim 16, wherein the retaining arm includes a slip-resistant surface positioned to engage the blood collection tube.

20. A blood collection device as set forth in claim 19, wherein the slip-resistant surface is textured.

* * * * *